United States Patent
Black

(10) Patent No.: US 7,128,692 B2
(45) Date of Patent: Oct. 31, 2006

(54) METHODS AND SYSTEMS FOR PROVIDING QUANTITATIVE ASSESSMENT AND RELAYING OF FIGHTER PERFORMANCE

(76) Inventor: John W. Black, 4860 W. Montara Cir., Las Vegas, NV (US) 89121

( * ) Notice: Subject to any disclaimer, the term of this patent is extended or adjusted under 35 U.S.C. 154(b) by 502 days.

(21) Appl. No.: 10/351,080

(22) Filed: Jan. 23, 2003

(65) Prior Publication Data

US 2003/0181290 A1 Sep. 25, 2003

Related U.S. Application Data

(60) Provisional application No. 60/373,776, filed on Apr. 18, 2002, provisional application No. 60/351,499, filed on Jan. 23, 2002.

(51) Int. Cl.
*A63B 21/00* (2006.01)
*A63B 22/00* (2006.01)

(52) U.S. Cl. .................. 482/8; 482/1; 482/9; 482/83; 482/84; 73/379.04

(58) Field of Classification Search ............... 482/1–9; 463/31, 36; 702/41, 149; 73/379.04
See application file for complete search history.

(56) References Cited

U.S. PATENT DOCUMENTS

| | | | | |
|---|---|---|---|---|
| 4,763,284 | A * | 8/1988 | Carlin | 702/41 |
| 5,723,786 | A * | 3/1998 | Klapman | 73/379.04 |
| 6,139,432 | A * | 10/2000 | Watanabe et al. | 463/31 |
| 6,183,365 | B1 * | 2/2001 | Tonomura et al. | 463/36 |
| 6,611,782 | B1 * | 8/2003 | Wooster et al. | 702/149 |
| 6,746,371 | B1 * | 6/2004 | Brown et al. | 482/8 |

* cited by examiner

*Primary Examiner*—Glenn E. Richman
(74) *Attorney, Agent, or Firm*—Kirton & McConkie; Michael F. Krieger

(57) ABSTRACT

The present invention features various systems and methods for assessing, measuring, quantifying, and/or relaying athlete performance information, and particularly performance information relating to fighters or boxers. More particularly, the present invention relates to utilizing such technology as modified ergometer based technology, optical sensor and motion analysis technology, accelerometers, and hydraulic meters for the measuring and/or improvement of the performance of fighters, for the facilitating of recruiting efforts, and/or for the enhancement of boxing matches.

16 Claims, 6 Drawing Sheets

METHODS AND SYSTEMS FOR PROVIDING QUANTITATIVE ASSESSMENT AND RELAYING OF FIGHTER PERFORMANCE

RELATED APPLICATIONS

This application claims priority to U.S. Provisional Application Ser. No. 60/351,499, filed Jan. 23, 2002, and entitled, "Methods and Systems for Obtaining and Providing Information Relating to Fighter Performance." This application also claims priority to U.S. Provisional Application Ser. No. 60/373,776, filed Apr. 18, 2002, and entitled, "Measuring the Power and Endurance of Boxers."

BACKGROUND

1. Field of the Invention

The present invention relates to systems and methods for obtaining and providing information relating to the performance of fighters. More particularly, the present invention relates to utilizing such technology as ergometer based technology, optical motion analysis technology, accelerometers, and hydraulic meters for the measuring, improvement, and/or relaying (of information) of the performance of fighters.

2. Background of the Invention and Related Art

In the sport of boxing, technique, speed, power, and endurance are critical factors. While a proper boxing technique may be taught by an experienced trainer, methods currently available to boxing coaches are limited in their ability to quantify how hard a particular fighter hits and what the limitations are of the fighter's endurance. Typically, the power and endurance of a fighter is only expressed relative to the competition that the fighter has encountered. As such, it is difficult for a trainer to improve the power and endurance of a boxer.

Current methods and/or devices used to measure the power and endurance of a boxer have left the boxing community dissatisfied. For example, one device requires the boxer being tested to hit in the same location from the same angle each time to avoid variances. However, in reality two punches with equal power rarely land in the same location. Thus, the measurement taken by the traditional device is typically viewed as being inaccurate.

The speed and power of a fighter may be evaluated visually compared to the competitor's speed and power. However, the visual evaluation can provide inaccurate results. For example, a fighter may look like he can hit because he wobbles his opponent with every punch, but his opponent just may not be able to take a good punch.

One device currently available to boxers requires an individual to sit on a seat and to set the speed at which the individual is able to turn pedals/handles with his/her arms. A dial indicates the rpm that is achieved when the individual turns the handles. The dial also allows for an indication of the top rpm and the amount of time it takes to reach the maximum rpm. While the device is available, boxers only use the device to condition their arms and shoulders. As such, the device may be used to condition, but does not quantify performance.

A fighter's performance and ability can also be difficult to quantify for the viewer of a boxing match. Current methods include the providing of pre-fight statistics to spectators, wherein the pre-fight statistics include the win/loss record of the fighter, the physical characteristics of the fighter (e.g., the fighter's height, weight, age, size of their neck, chest, biceps, waist, and reach), and a punch count. While these statistics may provide information to spectators, the information is typically not as helpful at it may initially appear. For example, while the win/loss record of a fighter often looks good on paper, it is oftentimes misleading. A fighter may have a record of 10-0 with 10 KO's. Promoters know that this kind of record will cause fans to fantasize that the fighter is a dangerous puncher and to accept him as a credible opponent. However, what goes unknown to the public is that all of the opponents of the fighter have lost most of their fights, and all by a knockout. As such, in the sport of boxing, managers and promoters are able to pick opponents throughout the boxer's career, build up a misleading record, manipulate the ratings, and deceive the fans.

To enhance the boxing match, a system of counting punches was developed. In accordance with the system, the count for jabs thrown, total punches thrown, punches landed, and the percentage landed are provided at the end of each round. Typically, a correlation exists between the punch numbers and the winner of the match. Therefore, before a fight, a pattern recognition by fight commentators is typically limited to a comparison of which fighter has thrown the most punches and jabs in previous fights.

Traditional devices and methods are unable to reliably quantify or measure the speed, power, and endurance of fighters. As such, it would be an improvement in the art to reliably and accurately obtain and provide information relating to the performance of fighters.

SUMMARY AND OBJECTS OF THE INVENTION

The present invention relates to systems and methods for obtaining and providing information relating to the performance of fighters. More particularly, the present invention relates to utilizing such technology as ergometer technology, optical motion analysis technology, accelerometers and hydraulic meters, each with the ability to electrically transmit or relay various information relating to the performance of their users, such as power curve readouts, to an appropriate end device, such as handheld devices, TV's, computers, etc. for the measuring and/or improvement of the performance of fighters, for the facilitating of recruiting efforts, and/or for the enhancement of boxing matches.

In one exemplary embodiment, the present invention features a fighter performance device modeled after an ergometer, wherein the device simulates various punching situations, as well as the performance of the fighter in these situations and over time. The results of the fighter performance information obtained is then relayed to a coach or trainer for evaluation.

In another exemplary embodiment, the present invention features an optical fighter performance device that uses optics to assess, measure, quantify, and relay fighter performance information. The optical technology used functions to measure fighter performance information, while known processing technology processes the received signals into quantified, readable data. This data is then relayed to various parties as desired.

In still another exemplary embodiment, the present invention features an accelerometer fighter performance device that comprises a plurality of accelerometers or accelerometer array mounted all perpendicular to one another such that they can measure accelerations in three degrees of freedom. The data captured from the accelerometers is processed by a computer and relayed as desired.

While the systems and methods of the present invention have proven to be particularly useful in the area of boxing, those skilled in the art can appreciate that the systems and methods can be used in a variety of different applications, such as in the areas of martial arts, fitness workouts, and other such areas. These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1 through 6, is not intended to limit the scope of the invention, as claimed, but is merely representative of the presently preferred embodiments of the invention.

The presently preferred embodiments of the invention will be best understood by reference to the drawings wherein like parts are designated by like numerals throughout.

In addition, the following disclosure of the present invention is grouped into two subheadings, namely "Exemplary Operating Environment" and "Quantifying and Relaying Fighter Performance Information." The utilization of the subheadings is for convenience of the reader only and is not to be construed as limiting in any sense.

Exemplary Operating Environment

Figure 1:
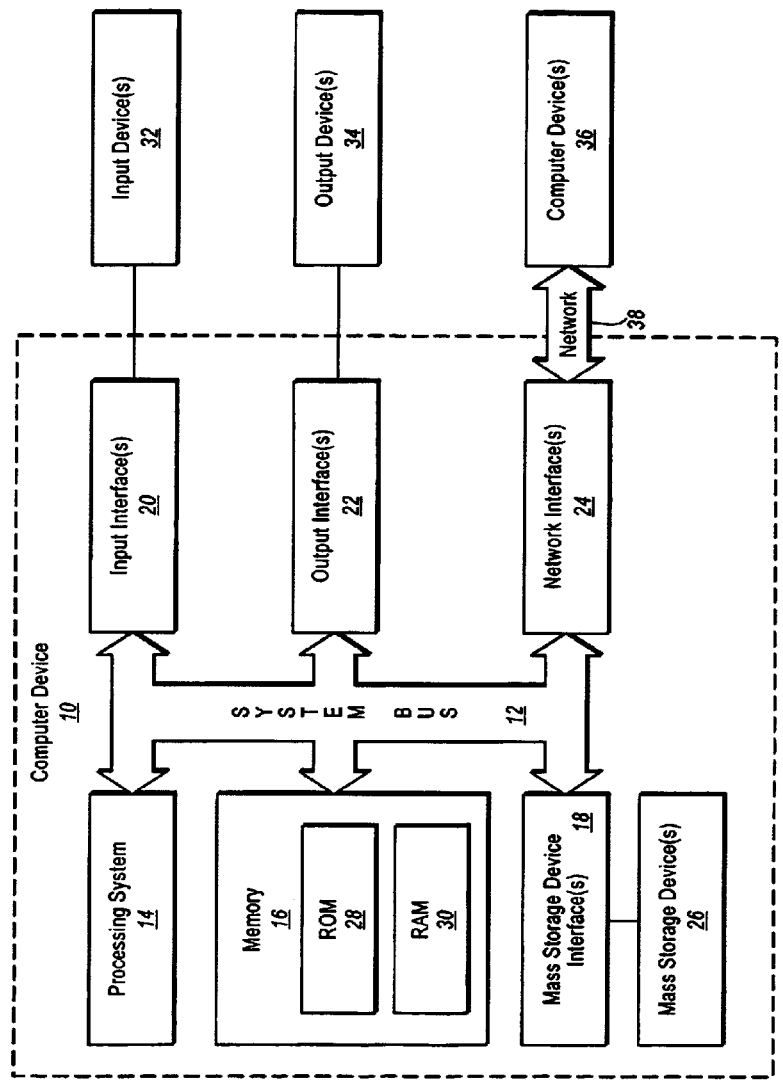
FIG. 1 illustrates a representative system that provides a suitable operating environment for use in association with embodiments of the present invention.

FIG. 1 and the corresponding discussion are intended to provide a general description of a suitable operating environment in which embodiments of the present invention may be implemented to obtain and/or provide information relating to fighter performance. One skilled in the art will appreciate that the invention may be practiced by one or more computing devices and in a variety of system configurations, including in a networked configuration.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative system for implementing the invention includes computer device 10, which may be a general-purpose or special-purpose computer. For example, computer device 10 may be a personal computer, a notebook computer, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), a firewire (IEEE 1394), or another interface.

One or more output interfaces 22 may be employed to connect one or more corresponding output devices 34 to system bus 12. Examples of output devices include a monitor or display screen (e.g., a television or other monitor), a speaker, a printer, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Those skilled in the art will appreciate that embodiments of the present invention may be practiced in networked computing environments with many types of system configurations that embrace the quantifying and relaying or obtaining and/or providing of fighter performance information. For example, one system may include a networked environment that comprises one or more clients connected to a server via a network. Moreover, embodiments in accordance with the present invention also include a multitude of clients throughout the world connected to a network, where the network is a wide area network, such as the Internet. The manner for quantifying and relaying or obtaining and providing fighter performance information is discussed below.

Quantifying and Relaying Fighter Performance Information

The present invention describes a method and system for assessing and quantifying fighter performance characteristics, and relaying such information as desired to an intended beneficiary, such as a coach, trainer, attendees of an event, TV audience, or any others. Fighter performance characteristics may be defined as speed, power, acceleration, agility, endurance, fatigue, or any other type of characteristic or element of a fighter's persona during a punching oriented workout or actual bout. Fighter performance information may be defined as any type of information that is assessed and quantified by the devices and systems of the present invention, such as power curve, speed, endurance, etc. Fighter performance information is obtained and relayed using advances in the art, namely an ergometer-type fighter performance device, an optical fighter performance device, and an accelerometer fighter performance device, each of which are described below in relation to their corresponding Figures.

In accordance with the several exemplary embodiments of the present invention, tools, systems, and devices, are provided that enable coaches, trainers, third parties, and others to monitor the biomechanics and the development of greater and more consistent power during a workout or an actual bout. The performance devices described herein function to measure and quantify the current ability and improvement of fighters, as well as to relay such information as desired. The present invention also functions to, among others, facilitate recruiting efforts and to enhance boxing matches. Furthermore, the information made available in accordance with the present invention provides a dramatic improvement in resources for coaches and trainers, such as providing better power and fitness evaluations, safer and more competitive matchmaking, and more drama and excitement.

Feedback of performance data, such as the power of a fighter, is invaluable to coaches and is a proven incentive to athletes in training. There are several uses for such feedback. For example, the speed and power is monitored from punch-to-punch and round-by-round, since acceleration of speed is a function of power. A trainer evaluates and/or corrects a boxer's form for better mechanics, since form and leverage transferring the mass of his body are related to power. A correct mix of aerobic and anaerobic conditioning is evaluated for the first round versus the sixth or other round to test the boxer's power and endurance. The coach evaluates recovery rates during one-minute rest periods between rounds. The first 15 seconds of the second round is compared to the last 15 seconds of the first round. The cumulative readouts for the rounds are compared. The fitness buff in the garage checks each punch and the cumulative output after each round for developing power and endurance. A handheld power readout device, such as a computer device, is programmed to receive data electronically from any fluid filled training apparatus and/or provide specific and cumulative data for the coach monitoring the workout.

A handheld readout device provides and/or stores valuable performance information. The force exerted by a straight punch, hook or uppercut anywhere on a fluid-filled training device is transmitted wirelessly or otherwise to a handheld device. The device is programmed to record the force of individual punches and the cumulative force by round and workout. The data is stored by boxer and/or by date. A comparative analysis by date is accessible for each boxer for training purposes.

In one embodiment, the handheld device provides base line power curves and measures and records improvement in power and endurance. Coaches monitor power, and work on improving training regimens. The device offers information for developing optimal strategies for specific opponents more scientifically.

In a further embodiment, a computer program used that provides additional information to facilitate preparing a game plan or strategy for specific opponents. For example, performance patterns are important factors in the sport of boxing. Pattern recognition software provides performance patterns of boxers to coaches during training. Embodiments of the present invention embrace a device that recognizes and displays patterns of boxers' power, which can differ during the workout, when he turns southpaw, and/or can differ in a particular round. As such, the round when his fighter is the most vulnerable is revealed.

Patterns of power from round to round inform a trainer the number of rounds his fighter is ready to fight. He may be training a six-round fighter who has been offered his first ten-round main event. Thus, it is critical to recognize the performance patterns before the fight.

In accordance with embodiments of the present invention, boxing trainers use methods to analyze their opponents, see the tendencies of how often they lead, what they like to lead with, how they react to different leads, how much time between their moves, how often they counter different leads, when they counter, and what they counter with, and the like. Trainers and fighters are able to be one step ahead of their opponent in planning how to fight a fight that could have a potential value of millions of dollars, because of knowing the probabilities of what the upcoming opponent like to throw and when.

In accordance with embodiments of the present invention, a trainer is able to measure a fighter's performance and to improve the performance. Base lines are recorded, and improvement is tracked in acceleration curves (e.g., speed and power), and optimal strategies for specific opponents are offered. Embodiments of the present invention provide trainers an extra edge in training and preparing for a fight.

Imagine seeing Mike Tyson score an incredible knockout of a 6'5" opponent who weighed 250 pounds. Instantly, a trainer touches his electronic pen to a screen and everything about that knockout becomes recorded data. The fight data that came directly from the number and types of punches thrown by both Tyson and his opponent are preserved. Every statistical piece of information about that fight gives you a reference not only to what it was, but also when and where it occurred. All of the relevant information may be dumped into an application that deciphers the information, looks for patterns within that data and responds to questions.

Generally, it is estimated that 180 punches are thrown in an average round. Each round generates volumes of statistics, such as the number and type of punches landed, which punches were thrown, who led with what punch or combination, and whether the lead was countered and by what punch. In one embodiment, the application employs data mining technology to interpret the information from each round. It may also manipulate data from past fights and feed back fight strategies to his trainer for training purposes.

Data mining technology involves the use of computers to automatically identify and find interesting patterns from a large amount of data.

The application takes a pattern representing fight circumstances and studies that pattern looking at all possible combinations. Every statistical pattern of leads, counterpunches, and punch combination is analyzed. The results are presented in an easily understood manner. The application further takes the user automatically to the most interesting pattern, giving the competitive edge that every fighter, trainer, manager and promoter is desiring.

As a result of embodiments of the present invention, trainers are informed of patterns, such as angles, parrying jabs, slipping inside and/or outside the jab, and the frequency of the patterns to exploit moves and strategies. In one embodiment, the application enables the boxer and his trainer to analyze these patterns or "styles" and to break down all of the opponent's moves, put them together as a unit, and see how the boxer should react. Against another fighter with a similar style, the application indicates, for example, that a prospective opponent likes to lead with single jabs to keep him outside. It further indicates what a fighter is doing well at, such as keeping an opponent outside until he gets softened up and then he moves inside. The trainer is able to recognize that he has to develop moves around the opponent's jab in the early part of the fight.

As provided by embodiments of the present invention, meaningful criteria are obtained and provided. Patterns of speed and power from round to round provide a trainer with an enormous amount about the number of rounds his fighter was ready to fight. It also informs the trainer of the round when he and his prospective opponent were or will be the most vulnerable. Such statistics provided during a televised fight using sports enhancement technology significantly adds to the viewer's experience of drama and enjoyment of a fight. Pattern recognition is provided of the fighter's moves and the fluctuations in his speed and power punch by punch, minute by minute, and round by round. This data may be used in accordance with embodiments of the present invention to pick fights and/or develop a fight strategy.

Ergometer-Type Fighter Performance Evaluation Device

The following is a discussion relating to a power curve system or device. An exponential power curve (one which reaches a dramatically steep gradient very quickly) is the kind of power curve the ideal boxer's punch expresses when measured. Measuring indicates that his acceleration is so quick that he reaches maximum speed with a very short punch. A boxer with that kind of acceleration knock outs with an eight inch punch or shorter, as opposed to hitting an opponent at the end of his punch with an almost fully extended arm. The boxer who takes the full length of a punch to reach maximum acceleration only hits his hardest at the end of his punch. The boxer with maximum acceleration in a short punch is a very dangerous fighter inside. He has maximum power when fighting inside with very short punches.

One exemplary embodiment of a system/device disclosed herein measures the power curve of a boxer's straight punches. For these purposes, power is the boxer's mass (weight and mechanical efficiency) times the acceleration (rate of increase in the speed of his fist). In contrast to traditional methods where the motion is rotary, one embodiment allows for the pushing straight out horizontally (simulating a straight punch with one hand) while allowing for the pulling back the "punch" just finished with the other hand. The user stands (simulating a boxer's stance) at the device, enabling him to turn his whole body behind the "punch." To maximize power, he may be forced to turn his shoulders in sync with the forward extension of the arm throwing the punch. He "learns" to use the mass of his body in accelerating one side while pulling back on the other side, simulating a series of straight one-two punches. A horizontal mechanism, set with similar speed settings, may be mounted on a vertical apparatus adjustable for the height of the user. A timer is used to measure the time it takes the user to reach his maximum speed.

Embodiments of the present invention provide a variety of advantages over traditional techniques, including:

1. Once the height of the device is adjusted for the user, the neuromuscular patterns (grooves) established are identical to straight punches executed by boxers.

2. To achieve maximum force, it forces the user to train the large muscle groups of his hips and torso to work in sync with the smaller muscle groups of his shoulders and arms, (turning or pivoting his body with his punches) as opposed to "arm" punches.

3. The position of the user is standing on his feet, as in boxing, not sitting as with traditional methods.

4. The rpm and timer are designed to provide a power curve readout.

5. The boxer is forced to develop more initial acceleration in the pivot, or turning, of his body to compensate for the reduced mechanical advantage of his arms at the initial part of his punch. As a boxer's arm is extended, he has more strength because of the mechanical advantage, similar to the added strength he has at the top of a bench press compared to when he is at the bottom, pushing the bar up from his chest.

6. The device enables the user to "throw a series of right-left straight punches" in five second bursts with a five second rest in between for three minute sets with a minute rest in between sets. The computer readout indicates his performance during each three-minute round. The coach may then evaluate how well he recovers between rounds, and determine the round when he begins to fade. This would indicate the number of rounds his conditioning would enable him to compete before his power begins to fade.

7. With some embodiments, the motion is back and forth in a straight line horizontally, and the handles are designed so that the fists can be turned over, pronated (horizontal), at the very end of the stroke identical to the way they are in boxing.

8. With some embodiments, one arm can be worked at a time in a series of straight punches, practicing jabs and a series of straight right hand punches.

Currently existing in the art is a machine manufactured and sold by Cybex, Inc. called an Ergometer. The machine is designed to provide both upper and lower body strengthening and conditioning. To use the machine, the user sits in an upright position facing three dials. The first dial measures rpm, the second dial measures the duration of time, and the third is a dial by which the user can adjust and set the crank speed or resistance. Encased in the housing of the Ergometer, in front of the user, are three dials mounted in a mechanical apparatus having an axel in the center. Attached to the axel are two bars at the end of which are handles for grasping. Essentially, the machine comprises a bicycle wheel mounted within the housing having a sprocket attached thereto. However, instead of foot pedals for pedaling with the legs and feet, the machine employs two handles which the user may grasp for turning the wheel with his or her arms and hands. When the user turns the apparatus, the hands move in a circular motion on each side of the apparatus as the user maintains a stable sitting position. The user can adjust and set the crank speed for high resistance and low rpm or low resistance and high rpm. The Ergometer provides a great upper body exercise device for overall body conditioning, and particularly the shoulders and arms.

Upper body conditioning and strength is also critical to boxers. The main focus in the trainer of a boxer is to develop good form and increase the output of kinetic energy. Good form maximizes mechanical leverage and mass. Once good form is established and stable, to improve upon it is very difficult. A good fighter is continuously aware of and trying to improve form. Although slight modifications or improvement to a fighter's form are always possible, once the fighter's form is stable and consistent, attention typically turns to developing or maximizing the kinetic energy in executing that good form. One device used to evaluate and improve form is a camcorder, wherein the boxer may study his or her movement in slow motion, or frame by frame.

The fighter performance device of the present invention is a modified design of the Ergometer, specifically adapted for use within the boxing environment, and specifically designed to be used to improve a fighter's kinetic energy. The present invention takes this concept a step further by providing means by which to measure and relay various aspects of a fighter's performance and/or condition. For example, the fighter performance device is capable of measuring the kinetic energy of a fighter, thus allowing the fighter to be aware of and monitor improvements in this area.

Figure 2:
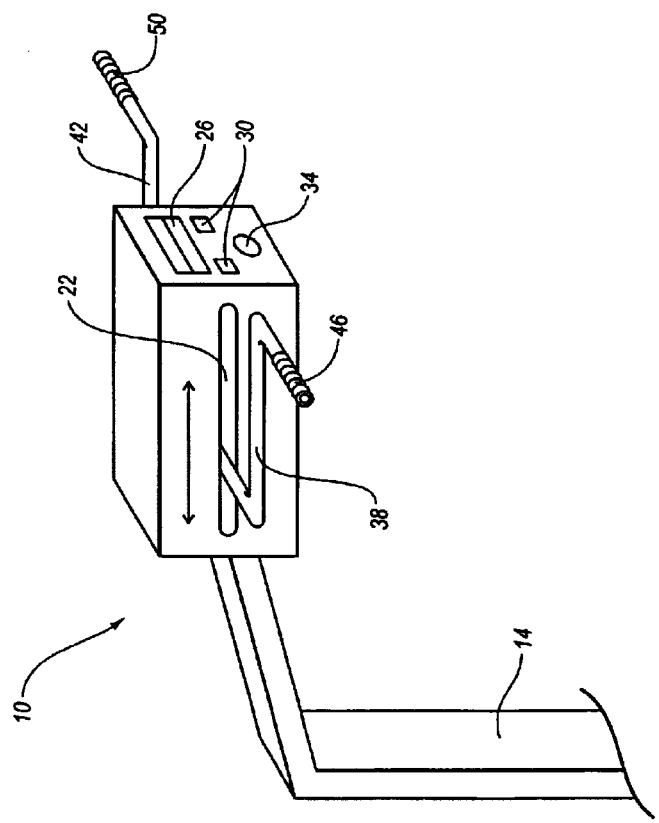
FIG. 2 illustrates an ergometer-type fighter performance device having horizontal bi-directional movement to resemble or simulate a straight punch.

With reference to FIG. 2, shown is one exemplary embodiment of fighter performance device 10. It should be noted that the designs depicted or illustrated in the drawings are merely exemplary, and are not to be considered limiting. Other design configurations are contemplated and should be apparent to one of ordinary skill in the art.

Fighter performance device 10 comprises an adjustable (in any vector) base support 14 that gives support and stability to the entire assembly, and particularly upper assembly module 18, which comprises the mechanical assembly used to execute the function of fighter performance device 10, as well as to support extension arms 38 and 42 and the directional motion of these. Base support 14 may be configured or designed in any shape and size, as long as it is designed to properly support and stabilize device 10 during use.

As shown, extension arms 38 and 42 extend from upper assembly module 18 in opposing directions and have attached thereto handles 46 and 50, respectively, that a user may grasp to actuate device 10. In this particular embodiment, extension arms 38 and 42 are contained and allowed to move in an opposing bi-directional manner within a horizontal or substantially horizontal slot 22. As such, device 10 provides for elevated horizontal motion. It is this motion that simulates the motion of a fighter while throwing a straight-line punch. Essentially, extension arms 38 and 42 move back and forth opposite one another within slot 22 upon the user grasping handles 46 and 50 and exerting the force required to actuate device 10, which is explained in greater detail below.

Upper assembly module 18 further comprises an adjustable resistance assembly (not shown) that is used to provide selective resistance to extension arms 38 and 42. The resistance assembly adjusts to allow the user to achieve high resistance and low rpm, low resistance and high rpm, or any combination of these. Thus, as a user is undergoing an evaluation or performance session, the resistance can be set, altered, and/or varied as needed or desired. The various types of resistance assemblies that may be used are many, and are not specifically described herein, but will be apparent to one of ordinary skill in the art.

In this particular embodiment, unlike prior art ergometer devices, there is not seat. The fighter (or nay other athlete wishing to perform the same conditioning and evaluation) preferably positions himself in a standing position so that handles 46 and 50 are at substantially the same vertical elevation as the user's (or fighter's) shoulders. In this position, the user is more closely simulating the position he or she would be in as a fighter preparing to throw various punches against an opponent. The user then grasps handles 46 and 50, and, while pushing on one, simultaneously pulls on the other in a horizontal bi-directional manner. As device 10 is actuated by the user, one arm extends outward with the hand following in line straight out, while the other arm is brought inward with the hand following in line straight back. Since the user is in a boxer's position and simulating similar motions that would be experienced during a punch, the hips and upper body, especially the shoulders, of the user tend to pivot. For example, if the right arm and hand are extended outward in front of the right shoulder, the right shoulder and upper body tend to pivot or rotate counter clockwise (from a top reference point of view) in sync with the hand. Correspondingly, as the left arm and hand are brought inward by pulling on the corresponding handle, the left shoulder and upper body are further urged or further tend to rotate or pivot counterclockwise. Once the linear bi-directional motion is switched so that the left arm and hand are extending outward and the right arm and hand are being brought inward, this causes the hips and upper body to have a tendency to rotate or pivot clockwise. As such, this back and forth bi-directional linear movement by the arms and hands, as well as the resulting rotational movement of the hips and upper body, functions to force the body to work together in sync with each other for each punch (extension) and corresponding pull (retraction). Stated differently, this motion allows the mass (the weight), which is an element in the formula for assessing or quantifying kinetic energy, of the user to be maximized, assuming the user is trying to maximize the rpm of device 10. Maximizing mass allows the user to obtain the most power and to direct such power into his or her punch and ultimately to the opponent.

More specifically, the pushing or extension motion allows the user to simulate a straight-line punch, such as a jab or more powerful punch, while the simultaneous pulling of the opposite hand serves to simulate the tendency of the non-punching arm/hand to be pulled in towards the user's body. The pushing motion provided by device 10 allows the user to work on form and control while punching in a controlled environment, while at the same time allowing the user to monitor, assess, and improve the force or power of the punch, measured in output kinetic energy. On the other hand, the pulling motion provided by device 10 allows the user to focus on both the form of the non-punching hand during a punch, as well as to increase or improve the action and function or purpose of such motion to aid in and optimize the output power or energy of the punching hand. The pushing and pulling motions are highly correlated and each contribute to an improved punch, measured in terms of both power or kinetic energy and form. Of course, other quantifying measurements or assessments may be made through use of device 10, such as acceleration, strength, speed, timing, etc.

Figure 3:
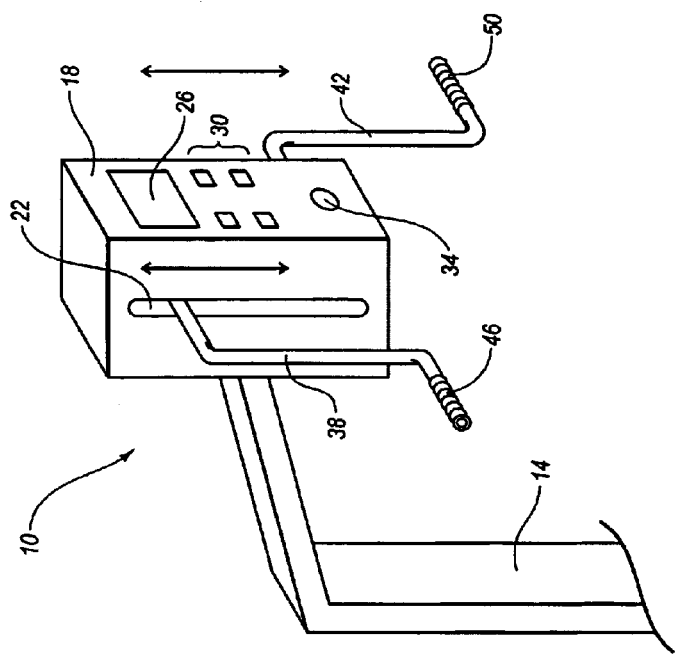
FIG. 3 illustrates an ergometer-type fighter performance device having vertical bi-directional movement to resemble or simulate an uppercut punch.
Figure 4:
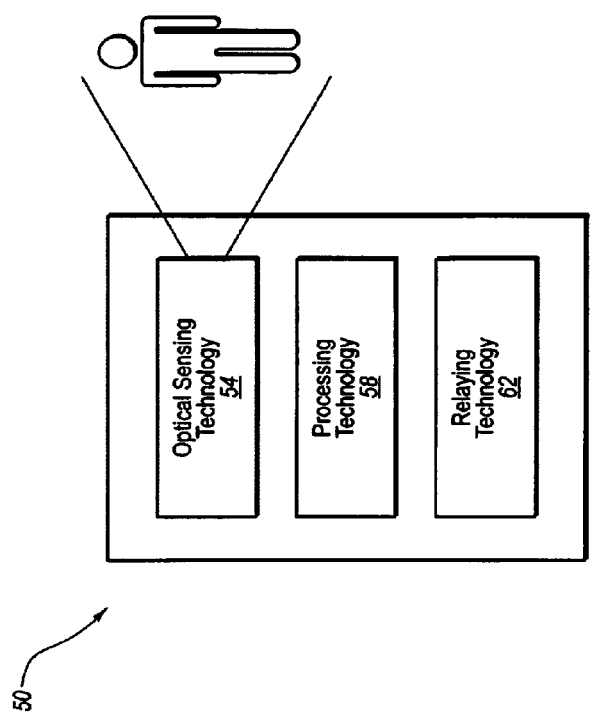
FIG. 4 illustrates a block diagram of an optical fighter performance device.

With reference to FIG. 3, shown is another exemplary embodiment, wherein fighter performance device 10 comprises similar components as those described above, except that extension arms 38 and 42, and associated handles 46 and 50, move in a vertical bi-directional manner. In this particular embodiment, the motion simulated is that of an uppercut by a boxer. Both the speed and the power curve of the user may be quantified and relayed, to assist in improving each of these.

While the above embodiments of fighter performance device 10 describe both horizontal and vertical linear bi-directional movement, other movements are also contemplated. For instance, movements over or corresponding to a spline or otherwise curved configuration may be advantageous to more precisely simulate the various types of punches, as well as to accommodate different user styles. As such, the present invention simulated motion is not to be limited to linear motion, but rather is intended to encompass any type of movement within its scope.

Fighter performance device 10 further comprises controllers for adjusting the device, as well as a plurality of readout devices to relaying, monitoring, and/or assessing current or stored performance, session, etc. information. For example, control device 34 may be used to vary the resistance of the device, while controller devices 30 may be used to control readout or display 26. Various information may be collected, contained or stored within, and communicated or relayed, such as the user's top speed, the length of time taken to achieve top speed, the acceleration achieved upon changing directions between a push/extension and a pull/retraction.

This type of information is valuable as it would allow the user, or a trainer, to evaluate the user during the course of the workout or simulation session. For example, the two baselines of maximum velocity and the time it took to reach the maximum velocity would provide the user or trainer with the user's power curve. Some fighters develop maximum power with a very short punch, while some fighters do not develop much power with a short punch, but need to hit you at the end of their punches to be effective.

The goal of a boxer is optimizing an exponential power curve in every punch. The present invention fighter performance device 10 functions to measure and quantify this curve relative to the performance of the user from using device 10, as well as to improve and provide valuable insight as to the user's form and mass (the pivotal rotation and movement of the user) during a punch. From the information obtained, the user could improve training techniques, methods, etc. through being made aware of high and low points of performance evidenced as a result of the performance from using device 10. Naturally, subsequent time spent using device 10 would allow the user or the trainer to measure and assess any improvements, digressions, etc.

In an exemplary embodiment, fighter performance device 10 would be an extremely valuable training device for a boxing coach. It would give a boxer a tremendous advantage fighting "inside" with short punches. In addition, power "outside" at the end of his or her stroke would also improve. Ideally, improvement of the speed and power of a boxer requires neurological training (e.g. awareness, reflexes, and speed) supplemented with strength training. The present invention fighter performance device 10, with an adjustable speed element, is capable of doing both.

Optical Fighter Performance Evaluation Device

The present invention further comprises an optical fighter performance device 50 that utilizes optical sensing technology 54 to measure the speed and rate of increase in speed (power curve) of a user's punch. In this particular embodiment, the optical performance device would be able to assess, measure, quantify, etc. various aspects related to a fighter's performance, process such information accordingly using known processing technology 58, and then relay any information pertaining to these to various third parties, such as several fans who are watching a boxing match from home on TV, through known relaying technology 62. The type of performance information assessed, quantified, and relayed by the present invention for each fighter would allow each person in receipt of such information to have access, on a round by round, punch by punch, or any other duration or instance basis.

Processing technology 58 is essentially described above and is well known in the art, but may also include any additional devices, systems, algorithms, etc. needed to convert the retrieved signals from optical sensing technology 54 into readable data. Moreover, relaying technology 62 is also well known and not specifically described herein.

The following discussion relates to broadcasting a boxing match. When satellite signals were converted from analog to digital technology, equipment prices dropped as did the cost per channel. Digital conversion spawned the direct-to-home broadcast market. Satellites may be used to solve broadband's last-mile problem of how to create a high-speed link beaming fights on the Internet into households. Satellites will offer another way for developing countries to climb onto the Internet highway and to receive a large selection of new content. For example, in Southeast Asia, home to 25 percent of the world's population, only 0.04 percent of the people use the Internet. As such, satellites will provide the necessary uplink.

Satellites provide broadband to both hard-to-reach areas and emerging markets, a boom for fight content involving boxers throughout the world. Television programming enables hundreds of broadcasters to satisfy the demand for content virtually everywhere in the world. A high volume of fight content flowing from boxing shows put on by promoters worldwide selecting fights in accordance with embodiments of the present invention enable a fight channel with unprecedented content, geographically and in quantity and quality, but with a new, honest, transparent, and more lucrative revenue model for everyone, especially the fighters.

Boxers, like performers in the entertainment industry, desire to maximize their return on their fights, whether from purses, a share of foreign television advertising revenue, royalties from streaming videos of live fights, or residuals each time films of their past fights are viewed. Every time a fight is viewed, residual income may be provided for years.

The contracts of promoters typically include language describing certain rights the boxers sell to the promoter. The promoter obtains these rights to be able to sell them to television or other broadcasting media. To sell them, the promoter buys the rights from the boxer. The promoter, as the event organizer, acquires control of these rights through his contract with the boxer. The boxers and their managers typically qualify that language by reserving the right to stream videos of their fight on the Internet in perpetuity.

In addition to a larger share of the pay-per-view revenue from millions of boxing fans in the world who view their fights online and from the domestic and foreign television advertising before, during, and after the fight, boxers, winners and losers, organizing fights in accordance with embodiments of the present invention realize significant residuals from repeated viewing online by thousands of fans who missed the fight or want to see it again. This is a great incentive for both fighters to put on a memorable and exciting fight. Repeated viewing of fights now creates a very significant revenue stream for fighters. Fans now have an opportunity to see them at any time at a reduced rate. This provides continuing value to many fights that would otherwise not be available to some fans, unless a friend taped the fight. They would have no television value as reruns.

Many undercard fights on championship shows are never shown on television, but were taped for televising in case one of the main event fighters is knocked out early. There are thousands of these fights in television film libraries, which previously were unavailable as revenue generators. There are also thousands which were televised, but which previously had no value as reruns.

Broadcasting is free television over the air. Narrowcasting is subscription and pay-per-view cable and satellite television. Now there is pointcasting—digital technology. Fiber optics and the modification of screens are already in every home computer today. Digital technology enables more information and more channels to come into our home. That's why the technology is referred to as the information superhighway. Pointcasting enables the boxing fan in Europe or Fiji surfing the Internet to watch television. It is now technically possible for him to hit the keyboard of his home computer and watch a fight in Las Vegas live on his computer screen. Soon television will be fully digital and receive wireless telecasts from satellites.

As provided herein, embodiments of the present invention create several revenue streams for fighters. There is advertising at all the fights on the boxing corner pads and ring mats, electronic signs and other advertising behind the ring seen by the TV and live audience, and hanging banners at the venue in view of the live audience. Different advertisements are inserted electronically into the screen and targeted to regional audiences. Pointcasting and targeting increases the advertising revenue dramatically at both big and small events.

At large events like a World Championship fight, the international companies have an interest in reaching the whole world by placing their advertising at the venue. With permission and revenue sharing with holders of the digital rights to the fights (the promoter), embodiments enable the fans in the targeted areas watching the fight to see their country's local beer company advertisement on the ring mats and corner pads on their screens.

Assume each sign costs an average of only $10,000 per title fight, times 150 countries, times 12 title fights per year, the revenue stream from advertising quickly adds up. This is for the big events. The smaller boxing shows with fighters from different countries benefit even more. Boxing fans watching a show with fighters on the card from Mexico, Brazil, and the U.S. will all watch the same picture, but the advertising signs are in different languages for different countries.

In accordance with some embodiments of the present invention, fans view fights in one of two ways, choosing a specific fight by selecting criteria in a drop-down menu, such as, gender, weight class, boxer name, opponent's name, a particular round, the results of fights, or the type of fighters.

Fans have their favorite weight classes, boxers, fights, and even memorable rounds. Thus, once a fan decides upon their favorites, selections are made and saved for future viewing. Repeated viewing by fans is a great source or residuals for fighters.

According to embodiments, fans are able to enjoy the excitement of real-time data on television during a fight to measure the speed and acceleration curves (power) of a fighter's punches relative to his opponent. When the fight is taped by trainers, managers and promoters, they are able to use it for later reference in matchmaking. Television pre-fight data reveals power patterns during each round in past fights in order for television sports programmers to make more competitive and exciting fights and avoid mismatches.

According to embodiments, audio is programmed so that the quality and up-close sound of punches landed correlates to the speed and acceleration readout on the television screen during the fight. The harder a punch lands, the louder it is. Fans are sensitive to the excitement of the powerful sound of punches when they sit at ringside. It adds to their enjoyment of the fight. There is more drama in a hard punch heard from up close. As such, drama is captured and enhanced, eliminating the need for some of the ringside chatter of television commentators.

Thus, according to some embodiments, power statistics and correlated audio during a televised fight significantly adds to the "Tale of the Tape," "CompuBox," and "Punchstats," and enhances the fans' experience of drama and enjoyment of a fight. Pattern recognition of the fluctuations in power, punch by punch, minute-by-minute, and round by round enhance the "Tale of the Tape," and an invaluable matchmaking tool is provided for broadcast media and for training in the gym. Power curves are displayed for fans during a fight.

The following are a few applications of sports enhancement and optical motion analysis technology used in accordance to embodiments of the present invention:

(1) Special purpose software applications combined with optical motion analysis technology to measure the acceleration curves and speed of boxers for improved performance of boxers during certain parts of training;

(2) Pattern recognition software applications to reveal patterns of speed and power of each boxer during training and as a fight progresses and thereby greatly enhance fans' enjoyment of a fight;

(3) Pattern recognition software applications to reveal power and execution patterns or "style" during the fight in order to make more competitive and exciting fights and avoid mismatches of power and styles;

(4) Analysis of patterns of power and styles in past fights against similar opponents to enable managers, matchmakers and promoters to pick fights in career planning; and (5) The selection of sparring partners, the preparation of training programs, and the development of a fight strategy.

Accelerometer Fighter Performance Evaluation Device

A boxing coach needs a device to tell him how hard a fighter hits and the limitations of the fighter's endurance. It goes without saying that power and endurance are just as important to a boxer as technique. However, it is difficult for a trainer to improve the performance of a boxer in terms of either power or endurance unless there is a way to assess, measure, and quantify such performance characteristics. As such, the present invention features a system and method for measuring and quantifying performance information relating to power in a punch (i.e., which punches were the hardest) and endurance sustained over a period of time (i.e., how long a fighter is able to continue hitting with the same level of power over a period of time).

As is well known, power does not equal force. Rather, power is the ratio of work over time, or equivalently, the force of an object multiplied by its displacement over time. The concept of force allows one to change an object's motion. The energy required to do that equals force times the displacement over which the force has been acting. The ability to transfer energy over time is what constitutes power. Power is reflected in the following equation:

$$\text{Power} = \underline{\text{work}} = \frac{\text{force} * \text{displacement}}{\text{time} \quad \text{time}}$$

Figure 5:
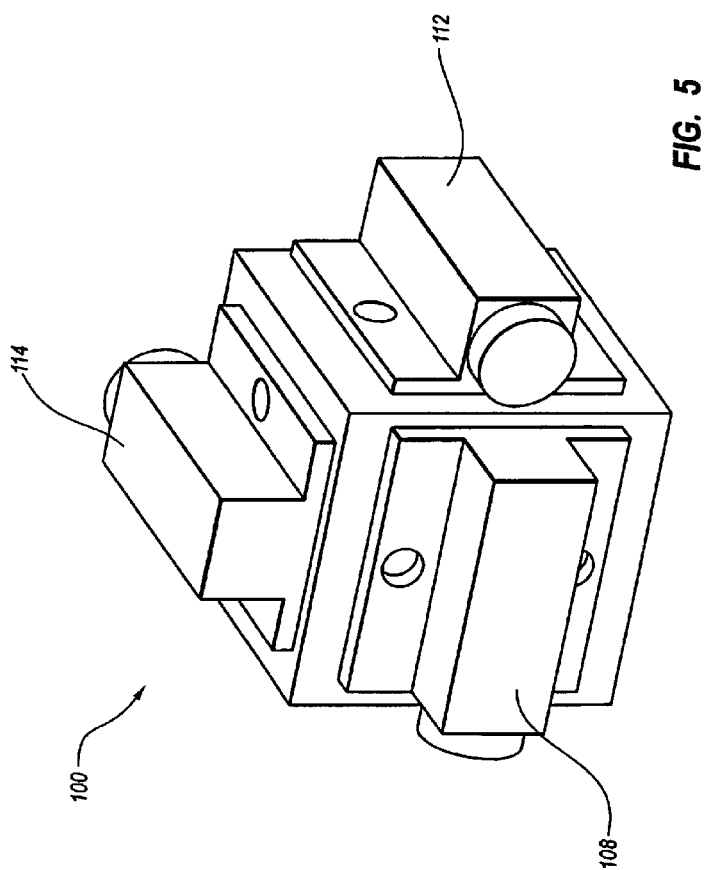
FIG. 5 illustrates an accelerometer fighter performance device.
Figure 6:
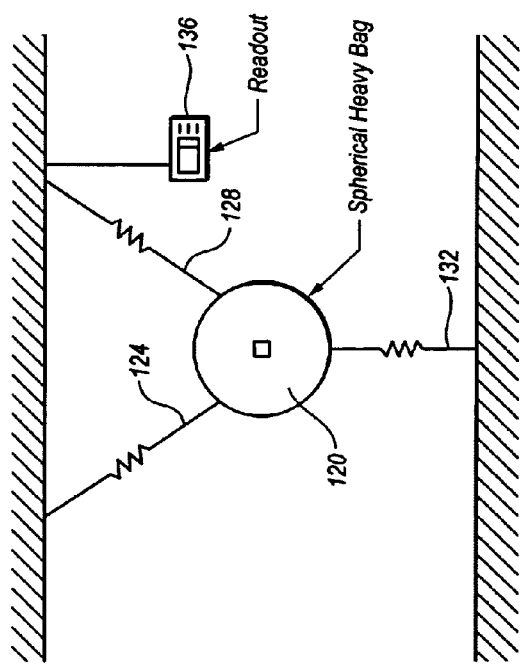
FIG. 6 illustrates a simulated punching environment.

FIG. 5 illustrates the present invention accelerometer fighter performance device 100 comprising a plurality of accelerometers or accelerometer array, preferably three, shown as accelerometers 104, 108, and 112, each mounted all perpendicular to one another such that they can measure accelerations in three degrees of freedom. The data captured from accelerometers 104, 108, and 112 is processed by a computer using special algorithms that result in an output of power and peak forces generated by the user.

In order to use the accelerometer device 100, it needs to be packaged appropriately. It has been previously identified that the use of accelerometers has proved to be difficult due to the precision required on the boxers behalf to locate their punch in the exact location time after time. This issue is a function of two problems: one, most accelerometer based systems only use one accelerometer and hence are only able to measure in one direction; two, the means by which the accelerometer is packaged was probably not conducive to repeatable means of measure.

Device 10 will be both repeatable and easy for the boxer and coach/trainer to use. The accelerometer array (group of three accelerometer mounted in the three degrees of freedom) will be packaged inside of a spherical bag, shown as spherical bag 120 in the simulated punching environment in FIG. 6. Spherical bag 120 will be supported by three tethered and elastic ropes, 124, 128, and 132, respectively, allowing spherical bag 120 to move in all three dimension or degrees of freedom. The reason for the spherical shape is that spherical bag 120 can be punched in any direction and at any point resulting in the majority of the punch being recorded by the instrumentation at the center of spherical bag 120. Once recorded, this information may be relayed to readout device 136.

Spherical bag 120 is preferably filled with fluid. Fluid is a wonderful medium for providing a hydraulic readout from a water-filled bag attached to a spout where the bag is filled at the top. The advantage of the contained fluid medium is that the same force of a punch anywhere on the bag provides the same power readout. In other embodiments, silicone or other mediums more closely resembling the viscosity of a body might be used. A fluid-filled stationary or cylindrical adjustable device may be designed to attach to the wall and simulate the hand pad positions of a mittman. The fluid-filled bag may also be hung from the ceiling or attached to the floor.

In an alternative embodiment, another option to measuring power to the one described above is to place one or more accelerometers inside the gloves of the boxer. Although a plurality may be used, preferably a single accelerometer in conjunction with a force transducer is placed within the padding in each glove to assess or measure and relay both power and peak force. The advantage in this system or arrangement is that it could be used anywhere on any training device and even in a bout situation.

It should be noted that the relaying attributes, characteristics, abilities, and uses discussed above for each of the other fighter performance evaluation devices discussed above are equally applicable to the accelerometer fighter performance evaluation device.

Thus, as discussed herein, the embodiments of the present invention embrace systems and methods for obtaining and providing information relating to the performance of fighters. More particularly, the present invention relates to utilizing such technology as ergometer technology, optical motion analysis technology, accelerometers and hydraulic meters with electrically transmitted power readouts to handheld devices for the measuring and/or improvement of the performance of fighters, for the facilitating of recruiting efforts, and/or for the enhancement of boxing matches.

The present invention may be embodied in other specific forms without departing from its spirit of essential characteristics. The described embodiments are to be considered in all respects only al illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A method of providing quantitative assessment and relaying of athlete performance, said method comprising the steps of:
   assessing athlete performance characteristics using an ergometer-type athlete performance evaluation device to obtain athlete performance information, comprising:
   measuring the acceleration of a punching motion;
   measuring the maximum velocity of a punching motion; and
   measuring the time it takes to reach the maximum velocity of a punching motion;
   quantifying said athlete performance information; and
   relaying said athlete performance information to an intended beneficiary using relaying technology.

2. The method of claim 1, wherein said step of relaying comprises relaying said athlete performance information to a coach/trainer beneficiary.

3. The method of claim 1, wherein said step of relaying comprises relaying said athlete performance information to a TV audience beneficiary.

4. The method of claim 1, wherein said step of relaying comprises relaying said athlete performance information to an event audience beneficiary.

5. The method of claim 1, wherein said step of relaying comprises relaying said athlete performance information across various computer networks, across various television networks, across various satellite networks, across a radio network, to a portable computer device, to a readout display on an evaluation device, and any other type capable of communicating said.

6. The method of claim 1 wherein the step of assessing athlete performance characteristics uses an ergometer-type athlete performance evaluation device comprising:
   an adjustable base support;
   an upper assembly module associated with said adjustable base support, said upper assembly module comprising a resistance varying assembly, a control center, and relaying technology;
   extension arms extending in opposing directions from said upper assembly module and outward toward a user, said extension arms moving in a resisted bi-directional manner to simulate straight-line punching of an athlete.

7. A method of providing quantitative assessment and relaying of athlete performance, said method comprising the steps of:
   assessing athlete performance characteristics using an optical sensing athlete performance evaluation device to obtain athlete performance information, comprising:
   measuring the acceleration of a punching motion;
   measuring the maximum velocity of a punching motion; and
   measuring the time it takes to reach the maximum velocity of a punching motion;
   quantifying said athlete performance information; and
   relaying said athlete performance information to an intended beneficiary using relaying technology.

8. The method of claim 7, wherein said step of relaying comprises relaying said athlete performance information to a coach/trainer beneficiary.

9. The method of claim 7, wherein said step of relaying comprises relaying said athlete performance information to a TV audience beneficiary.

10. The method of claim 7, wherein said step of relaying comprises relaying said athlete performance information to an event audience beneficiary.

11. The method of claim 7, wherein said step of relaying comprises relaying said athlete performance information across various computer networks, across various television networks, across various satellite networks, across a radio network, to a portable computer device, to a readout display on an evaluation device, and any other type capable of communicating said.

12. A method of providing quantitative assessment and relaying of athlete performance, said method comprising the steps of:
   assessing athlete performance characteristics using an accelerometer athlete performance evaluation device to obtain athlete performance information, comprising:
   measuring the acceleration of a punching motion;
   measuring the maximum velocity of a punching motion; and
   measuring the time it takes to reach the maximum velocity of a punching motion;
   quantifying said athlete performance information; and
   relaying said athlete performance information to an intended beneficiary using relaying technology.

13. The method of claim 12, wherein said step of relaying comprises relaying said athlete performance information to a coach/trainer beneficiary.

14. The method of claim 12, wherein said step of relaying comprises relaying said athlete performance information to a TV audience beneficiary.

15. The method of claim 12, wherein said step of relaying comprises relaying said athlete performance information to an event audience beneficiary.

16. The method of claim 12, wherein said step of relaying comprises relaying said athlete performance information across various computer networks, across various television networks, across various satellite networks, across a radio network, to a portable computer device, to a readout display on an evaluation device, and any other type capable of communicating said.

* * * * *